United States Patent [19]
Rao et al.

[11] Patent Number: 5,120,883
[45] Date of Patent: Jun. 9, 1992

[54] CATALYTIC PROCESS FOR PRODUCING $CCl_3CF_3$

[75] Inventors: V. N. Mallikarjuna Rao; Frank J. Weigert; Leo E. Manzer, all of Wilmington, Del.

[73] Assignee: E.I. du Pont de Nemours and Company, Wilmington, Del.

[21] Appl. No.: 749,785

[22] Filed: Aug. 26, 1991

[51] Int. Cl.$^5$ .................. C07C 17/10; C07C 19/08
[52] U.S. Cl. ................................................ 570/123
[58] Field of Search ............................. 570/123, 254

[56] References Cited

U.S. PATENT DOCUMENTS

| | | | |
|---|---|---|---|
| 1,380,067 | 5/1921 | Koch et al. | 570/254 |
| 1,432,761 | 10/1922 | Koch | 570/254 |
| 2,162,532 | 6/1939 | Flemming et al. | 570/254 |
| 2,469,290 | 5/1949 | Calfee et al. | 570/123 |
| 2,566,163 | 8/1951 | Calfee et al. | 570/123 |
| 2,639,300 | 5/1953 | Ruh et al. | 570/123 |
| 2,899,472 | 8/1959 | Bower et al. | 570/123 |
| 4,145,368 | 3/1979 | Sweeney et al. | 570/123 |

FOREIGN PATENT DOCUMENTS

| | | | |
|---|---|---|---|
| 402874 | 12/1990 | European Pat. Off. | 570/123 |
| 2529882 | 1/1984 | France | 570/254 |
| 3-58946 | 3/1991 | Japan . | |
| 1232623 | 2/1969 | United Kingdom | 570/123 |
| 1225956 | 3/1971 | United Kingdom . | |

OTHER PUBLICATIONS

Chem. Abst., 87(10), 68874q (1977).
A. A. Goleva et al., Russ. J. Phys. Chem., 44$^2$, 290–1 (1970).
M. Biswas et al., J. Macromol. Sci., Chem., A20(8), 861–76 (1983).
Chem. Abst., 80(25):145470q (1974).
Chem. Abst., 80(25):145469w (1974).
Organic Synthesis, Collective, vol. 3, pp. 685–690, (1955).
J. W. Hassler, "Activated Carbon", pp. 344–345, (1915).
M. Smisek et al., "Active Carbon", pp. 61–70, (1970).
F. J. Long et al., "The Effect of Specific Catalysts on the Reactions of the Steam-Carbon System", Proc. Roy. Soc., (1952), pp. 100–110.
R. B. Anderson et al., "Surface Complexes on Charcoal", J. Phys. Colloid. Chem., 51, pp. 1308–1329, (1947).
H. M. Frey, "A New Type of Catalytic Effect in the Oxidation of Carbon", Proc. Roy. Soc., (1055), pp. 510–518, (1955).
A. Blackburn et al., "Adsorption from Binary Liquid Mixtures: Some Effects of Ashin Commercial Charcoal", J. Chem. Soc., pp. 4103–4106, (1955).
F. J. Long et al., "The Catalysis of the Oxidation of Carbon", J. Chem. Phys., 47, pp. 361–378, (1950).

*Primary Examiner*—J. E. Evans

[57] ABSTRACT

A catalyic process is disclosed for producing $CCl_3CF_3$ from $CHCl_2CF_3$, $CH_2ClCF_3$ and/or $CH_3CF_3$ by chlorination at elevated temperature. Suitable catalysts for the process include carbon catalysts and catalysts wherein halides of certain metals (Zn, Cu, Cr, Ru, Rh, and/or Pt) are supported on carbon.

17 Claims, No Drawings

CATALYTIC PROCESS FOR PRODUCING CCL₃CF₃

FIELD OF THE INVENTION

This invention relates to the chlorination of aliphatic hydrofluorocarbons and hydrochlorofluorocarbons and more particularly to catalytic chlorination of hydrofluorocarbons and hydrochlorofluorocarbons.

BACKGROUND

British Patent Specification 1,225,956 discloses a process for the production of a chlorofluoroethane of the general formula $CH_{3-n}Cl_nCClF_2$ where n is 0 to 3 comprising the photochemical chlorination of 1,1-difluoroethane, which may contain less than 2% HF.

Belgian Patent Publication BE 844,822 as cited in CA87(10): 68874q discloses the photochemical chlorination of 1,1-difluoroethane in the gas phase to afford 1-chloro-1,1-difluoroethane.

There has been considerable interest in processes for the chlorination of aliphatic hydrofluorocarbons and hydrochlorofluorocarbons which avoid using expensive actinic light to effect such chlorination.

U.S. Pat. No. 2,644,845 claims a non-catalytic process for the chlorination or bromination of a 1,1,1-trihaloethane or -propane at a reaction temperature of between about 365° C. to 450° C. The chlorination of 1,1,1-trifluoroethane (HCFC-143a) at 497° C in 45% yield and with the following selectivities is shown in Example 6: 22% HCFC-133a, 33% HCFC-123 and 45% CF$_3$CCl$_3$ (CFC-113a)

U.S. Pat. No. 4,490,534 discloses a process for the preparation of 3-chloro-5-trifluoromethylpyridine derivatives comprising reacting a 5-trifluoromethylpyridine having a hydrogen atom at the 3-position with chlorine in the presence of a catalyst selected from the group consisting of activated carbon and a chloride of a metal selected from the group consisting of iron, antimony, copper and zinc.

1,1,1-Trichloro-2,2,2-trifluoroethane (i.e., CFC-113a or CCl$_3$CF$_3$) is a chlorofluorocarbon which has been used as an intermediate for the preparation of 1,1,1,2-tetrafluoroethane (i.e., HFC-134a or CF$_3$CH$_2$F). More particularly, 1,1,1-trichloro-2,2,2-trifluoroethane can be reacted with HF to afford 2,2-dichloro-1,1,1,2-tetrafluoroethane (i.e., CFC-114a or CF$_3$CCl$_2$F) which can then be converted to HFC-134a by hydrogenolysis. There is thus interest in developing efficient methods of producing CCl$_3$CF$_3$.

SUMMARY OF THE INVENTION

The present invention provides a process for producing 1,1,1-trichloro-2,2,2-trifluoroethane comprising the step of contacting a gaseous mixture containing at least one compound having the formula $CH_xCl_{3-x}CF_3$, where x is an integer from 1 to 3 and chlorine with a catalyst at a temperature of from about 225° C. to about 450° C., the catalyst being selected from the group consisting of carbon catalysts and catalysts of metal halide supported on carbon wherein the metal halide is selected from the group consisting of zinc chloride, zinc fluoride, copper chloride, copper fluoride, chromium chloride, chromium fluoride, ruthenium chloride, ruthenium fluoride, rhodium chloride, rhodium fluoride, platinum chloride, platinum fluoride and mixtures thereof.

DETAILS OF THE INVENTION

The present invention provides a process for the catalytic chlorination of a compound represented by the formula $CH_xCl_{3-x}CF_3$, wherein x is 1 to 3. Suitable organic starting materials include $CH_3CF_3$, $CH_2ClCF_3$, $CHCl_2CF_3$ and mixtures thereof. 1,1,1-Trifluoroethane is a preferred starting material. Preferably, the 1,1,1-trifluoroethane, 2-chloro-1,1,1-trifluoroethane, and/or 2,2-dichlorotrifluoroethane are converted to 1,1,1-trichloro-2,2,2-trifluoroethane without isomerization or disproportionation.

The catalyst for the chlorination may be composed of activated carbon alone or carbon with a chloride and/or fluoride of a metal selected from the group consisting of zinc, copper, chromium, ruthenium, rhodium, platinum and mixtures thereof. Under reaction conditions the metal halides may be in the form of mixed metal halides (e.g., a chlorofluoride).

Catalyst compositions consisting essentially of carbon are preferred and are considered particularly effective for chlorination even in the presence of HF. The carbon can be either washed or unwashed. Washing can be done with either water or acid. Washing, particularly with acids, reduces the ash content. Preferred acid-washed carbons contain 0.5 percent by weight or less, ash. Examples of acids which may be used in an acid wash include organic acids (e.g., acetic acid) and inorganic acids (e.g, HCl or HNO$_3$). Preferably hydrochloric acid or nitric acid is used. The acid treatment may be accomplished in several ways. A preferred embodiment is described as follows.

An activated carbon is soaked overnight with gentle stirring in a 1M solution of the acid prepared in deionized water. The carbon support is separated and washed with deionized water until the pH of the washings is about 3. The carbon support is then soaked again with gentle stirring in a 1M solution of the acid prepared in deionized water for about 12 to 24 hours. The carbon support is then finally washed with deionized water until the washings are substantially free of the anion of the acid (e.g., Cl⁻ or NO$_3$−), when tested by standard procedures. The carbon support is then separated and dried at about 120° C. A sample of this washed carbon is then soaked, if desired, in 1M HF prepared in deionized water for about 48 hours at room temperature with occasional stirring in an HF resistant container. The carbon support is separated and washed repeatedly with deionized water at about 50° C. until the pH of the washings is greater than 4. The carbon support is then dried at about 150° C., followed by calcination at about 300° C. prior to its use.

Commercially available carbons useful in the process of this invention include those sold under the following trademarks: Darcor ™, Nucharr ™, Columbia SBV ™, Columbia MBV ™, Columbia MBQ ™, Columbia JXC ™, Columbia CXC ™, Calgon PCB ™, and Barnaby Cheny NB ™. Preferred carbons include those prepared from plant-based materials that have been twice treated with acid, as described above, to reduce the ash content. The carbon support can be in various forms (e.g., powder, granules, or pellets).

If the catalyst composition contains one or more metals selected from zinc, copper, chromium, ruthenium, rhodium and platinum, the percentage of metal in the catalyst composition is not considered critical. Typically, the metal content is from about 0.1% to 30% by weight of the carbon.

In accordance with this invention, a gaseous mixture comprising (i) $CH_3CF_3$, $CH_2ClCF_3$ and/or $CHCl_2CF_3$ and (ii) chlorine is contacted with the catalyst at elevated temperature to produce $CCl_3CF_3$. An inert diluent such as argon, helium or nitrogen may be used in the chlorination reaction of the present invention. HF may also be present, particularly where catalysts consisting essentially of carbon are used. The amount of chlorine is not critical but is usually from 1.5 to moles, preferably from 3 to 4 moles, per mole of the organic starting material. The reaction temperature can range from 225° C. to 450° C., and is preferably from about 0° C. to 400° C. The contact time preferably ranges from about 5 to 60 seconds, and is typically about 30 seconds. Although the chlorination reaction of the present invention is usually conducted at atmospheric pressure, it may also be conducted under elevated or reduced pressure.

The chlorination reaction of the organic starting material may be conducted in any suitable reactor, including a continuous stirred tank reactor or a fixed bed reactor. It may be done in a batch or continuous mode. The reaction vessel should be constructed of materials which are resistant to the corrosive effects of hydrogen fluoride and chlorine such as Hastelloy ® nickel alloy and Inconel ® nickel alloy.

A gaseous mixture discharged from the reactor contains 1,1,1-trichloro-2,2,2-trifluoroethane, unreacted and/or partially reacted starting materials, hydrogen chloride and in some cases disproportionation product(s) and/or an inert diluent. HF may be present in some embodiments of the invention. The mixture may be refined using conventional means to obtain 1,1,1-trichloro-2,2,2-trifluoroethane. The recovered unreacted starting materials and less chlorinated products such as 2-chloro-1,1,1-trifluoroethane and 2,2-dichloro-1,1,1-tri-fluoroethane can be recycled to the reaction zone to improve the yield of 1,1,1-trichloro-2,2,2-trifluoroethane. 1,1,1-Trichloro-2,2,2trifluoroethane can be used to prepare 2,2-dichloro-1,1,1,2-tetrafluoroethane, which is an intermediate for the production of 1,1,1,2-tetrafluoroethane.

Practice of the invention will become further apparent from the following non-limiting examples.

EXAMPLES

Preparation of HCl-Washed Carbon—Catalyst A

A commercially available carbon (500 g, 6x16 mesh granules) was soaked for 120 hours with gentle stirring in 1M HCl. The carbon granules were collected on a fritted glass funnel and washed with deionized water until the washings were chloride free when tested with silver nitrate. The carbon granules were then dried at 20° C. for 60 hours, followed by calcination at 300° C. in air to obtain 468.8 g of dried calcined granules. The ash content and the elements present in the ash are shown in Table A.

Preparation of HCl/HF-Washed Carbon—Catalyst B

HCl-washed carbon (225 g, 6×16 mesh granules) prepared as described above was soaked for 48 hours at room temperature with occasional stirring in 1M HF (3 L) in an HF resistant container. The carbon granules were then placed in a 4 L HF resistant container on a steam bath and washed with deionized water (3 L portions, at about 50° C.) until the washings had a pH greater than 4.0. Finally the carbon granules were dried at 150° C. for 60 hours in air followed by calcination at 300° C. in air for 3 hours to obtain 216.6 g of dried calcined granules. The ash content and the elements present in the ash are shown in Table A.

TABLE A

| | Elemental Analysis of Carbon Granules | | |
|---|---|---|---|
| | ClW[a] (ppm) | ClFW[b] (ppm) | NAW[c] (ppm) |
| P | | | 320 |
| S | | | 3200 |
| Si | 760 | 74 | 905 |
| Cu | 18 | 3 | 12 |
| Mn | 1 | <1 | 11 |
| Fe | 65 | 25 | 90 |
| Ba | <1 | | 7 |
| Ca | 17 | | 755 |
| Zn | <3 | <1 | 5 |
| Mg | 21 | | 540 |
| K | 28 | | 7300 |
| Al | <240 | | <120 |
| Na | 250 | | 465 |
| Ti | <30 | 12 | 6 |
| Ash | 0.18% | 0.01% | 2.33% |

[a]HCl washed - Catalyst A
[b]HCl and HF washed - Catalyst B
[c]not acid-washed - Catalyst C In the following illustrative examples, all parts are by weight, all percentages are molar, and all temperatures are degrees Celsius unless otherwise stated. All reactions with hydrogen fluoride used commercial HF containing only trace amounts of water.

General Procedure for Chlorination

The reactor (a 0.5" IOD, 12" long Inconel ® nickel alloy pipe) was charged with the amount of catalyst as described in the following examples, and placed in a sand bath. The catalysts were treated and activated as described in the Examples.

The temperature was then decreased to the indicated value and, thereafter, the reactant flows were started. The flows were adjusted to give the indicated molar ratios and contact times in the Examples.

The reactor effluent was sampled on-line with a Hewlett Packard HP 5890 gas chromatograph using a 20' long, 1/8" diameter, column containing Krytox TM perfluorinated polyether on an inert support and a helium flow of 35 cc/minute. Gas chromatographic conditions were 70° C. for 3 min followed by temperature programming to 180° C. at a rate of 6° C./minute.

EXAMPLE 1

Chlorination Using Hcl and HF Washed Carbon

The general chlorination procedure described above was followed using carbon Catalyst B. A sample of the dried, acid-washed carbon catalyst (13.34 g, 30 mL of 6×16 mesh granules) was placed in the reactor and heated under a nitrogen flow to 350° C. over 1.5 hours. The temperature was reduced to 300° C. and the flow of chlorine started. After a half hour, the flow of $CF_3CH_3$ (143a) was also started. The molar ratio of chlorine to 143a was 4:1 and the contact time was 30 seconds. The reactor effluent was analyzed as described above. The results are shown in Table 1.

TABLE 1

| Time (hr) | Temp. (°C.) | % 143a[1] | % 133a[2] | % 123[3] | % 113a[4] | % 112a[5] | % HCE[6] |
|---|---|---|---|---|---|---|---|
| 2 | 300 | 53.8 | 1.6 | 0.4 | 39.3 | 2.0 | 1.5 |
| 3 | 325 | 26.1 | 1.0 | 0.3 | 67.5 | 2.7 | 1.0 |

TABLE 1-continued

| Time (hr) | Temp. (°C.) | % 143a[1] | % 133a[2] | % 123[3] | % 113a[4] | % 112a[5] | % HCE[6] |
|---|---|---|---|---|---|---|---|
| 4 | 350 | 6.8 | 0.4 | 0.1 | 88.8 | 2.1 | 0.4 |
| 5 | 375 | 0.5 | <.1 | <.1 | 95.3 | 1.8 | 1.1 |

[1] 143a = $CF_3CH_3$
[2] 133a = $CF_3CH_2Cl$
[3] 123 = $CF_3CHCl_2$
[4] 113a = $CF_3CCl_3$
[5] 112a = $CClF_2CCl_3$
[6] HCE = $CCl_3CCl_3$

Minor amounts of other products including $CClF_3$, $CCl_2F_2$, and $CCl_2FCCl_3$ were also found.

EXAMPLE 2

Chlorination Using HCl Washed Carbon Catalyst A

The general chlorination procedure described above was followed using carbon Catalyst A. The dried, acid-washed carbon catalyst (13.22 g, 30 mL of 6×16 mesh granules) was placed in the reactor and heated under a nitrogen flow to 350° C. over 1.5 hours. The temperature was reduced to 300° C. and the flow of chlorine started. After a half hour, the flow of $CF_3CH_3$ (143a) was also started. The molar ratio of chlorine to 143a was 4:1 and the contact time was 30 seconds for all but the 7 hour sample, for which the contact time was 15 seconds. The reactor effluent was analyzed as described above. The results are shown in Table 2.

TABLE 2

| Time (hr) | Temp. (°C.) | % 143a | % 133a | % 123 | % 113a | % 112a | % HCE |
|---|---|---|---|---|---|---|---|
| 2 | 300 | 56.1 | 1.5 | 0.3 | 40.5 | 0.4 | 0.4 |
| 3 | 325 | 27.2 | 1.0 | 0.2 | 69.4 | 0.9 | 0.5 |
| 4 | 350 | 6.5 | 0.3 | 0.1 | 91.2 | 0.9 | 0.1 |
| 5 | 375 | 0.5 | <.1 | <.1 | 97.7 | 0.9 | — |
| 7 | 375 | 8.3 | 0.3 | 0.1 | 89.8 | 0.8 | <0.1 |

Minor amounts of other products including $CClF_3$, $CClF_2CH_2Cl$, $CCl_4$, and $CCl_2FCCl_3$ were also found.

EXAMPLE 3

Chlorination Using HCl Washed Carbon

The general chlorination procedure described above was followed. A PCB carbon catalyst (102.5 g) was soaked overnight in 2 L of 1M HCl. The carbon was collected on a fritted glass funnel and washed with 500 mL of deionized water. The soaking and washing procedure were repeated two more times. After the third soak and wash the carbon catalyst was washed with deionized water until chloride free as determined by testing with silver nitrate. The carbon was then dried at 120° C. for 60 hours in air, followed by calcination at 110° C. for 18 hours in air. A sample of the dried, acid-washed carbon catalyst (12.52 g, 30 mL of 4×10 mesh granules) was placed in the reactor and heated under a nitrogen flow to 350° C. over 1.5 hours. The temperature was reduced to 300° C. and the flow of chlorine started. After a half hour, the flow of $CF_3CH_3$ (143a) was also started. The molar ratio of chlorine to 143a was 4:1 except for the 5 hour sample where it was 8:1, and the contact times were as shown below. The reactor effluent was analyzed as described above. The results are shown in Table 3.

TABLE 3

| Time (hr) | Temp. (°C.) | Contact Time (sec) | % 143a | % 133a | % 113a | % 112a |
|---|---|---|---|---|---|---|
| 1 | 250 | 30 | 94.2 | 1.6 | 3.5 | <0.1 |
| 3 | 275 | 30 | 80.6 | 1.6 | 17.1 | 0.1 |
| 4 | 300 | 30 | 59.0 | 1.5 | 38.3 | 0.4 |
| 5 | 300 | 30 | 55.3 | 1.4 | 41.9 | 0.6 |
| 6 | 300 | 60 | 39.4 | 1.1 | 58.0 | 0.7 |
| 7 | 325 | 30 | 31.4 | 1.1 | 65.7 | 0.9 |
| 8 | 325 | 60 | 13.3 | 0.5 | 84.1 | 1.1 |
| 9 | 350 | 30 | 9.2 | 0.5 | 88.4 | 1.0 |
| 10 | 350 | 60 | 1.8 | 0.1 | 96.1 | 1.2 |
| 14 | 375 | 30 | 1.1 | 0.1 | 97.3 | 0.9 |
| 15 | 375 | 15 | 9.7 | 0.4 | 88.5 | 0.7 |
| 16 | 400 | 15 | 3.5 | 0.1 | 94.4 | 1.1 |

Minor amounts of other products including $CClF_3$, $CF_3CHCl_2$, $CCl_4$, and $CCl_2FCCl_3$ were also found.

EXAMPLE 4

Chlorination Using Unwashed Carbon

The general chlorination procedure described above was followed. An unwashed carbon catalyst, Catalyst C (13.17 g, 30 mL of 6×16 mesh granules), was placed in the reactor and heated under a nitrogen flow to 350° C. over 1.5 hours to remove water. The temperature was reduced to 300° C. and the flow of chlorine started. After a half hour, the flow of $CF_3CH_3$ (143a) was also started. The molar ratio of chlorine to 143a was 4:1 and the contact times were as shown below. The reactor effluent was analyzed as described above. The results are shown in Table 4.

TABLE 4

| Time (hr) | Temp. (°C.) | Contact Time (sec) | % 143a | % 133a | % 113a | % 112a | % HCE |
|---|---|---|---|---|---|---|---|
| 1 | 300 | 30 | 57.1 | 1.5 | 39.7 | 0.6 | <0.1 |
| 3 | 325 | 30 | 27.7 | 1.0 | 65.9 | 2.5 | 1.3 |
| 4 | 350 | 30 | 6.5 | 0.3 | 89.9 | 1.9 | 0.4 |
| 6 | 375 | 30 | 0.5 | <0.1 | 96.4 | 1.5 | 0.7 |
| 8 | 375 | 15 | 7.2 | 0.3 | 90.0 | 1.4 | <0.1 |

Minor amounts of other products including $CClF_3$, $CF_3CHCl_2$, $CCl_4$, and $CCl_2FCCl_3$ were also found.

EXAMPLE 5

Chlorination Using $ZnCl_2$/Carbon

The general chlorination procedure described above was followed. A solution of $ZnCl_2$ (20.44 g) in water 75 mL) was poured over 40 mL of commercial carbon granules (Girdler 411, 0.32 cm pellets). The resulting mixture was allowed to stand at room temperature for 1 hour and was then placed in a vacuum oven at 110° C. for 16 to 24 hours to remove the water. A sample of this catalyst (22.8 g, 30 mL) was placed in the reactor and heated under a nitrogen flow to 350° C. over 1.5 hours. The temperature was reduced to 250° C. and the flows of chlorine and 143a started. The molar ratio of chlorine to 143a was 4:1 except for the 5 hour sample where it was 8:1. The contact time was 30 seconds. The reactor effluent was analyzed as described above. The results are shown in Table 5.

TABLE 5

| Time (hr) | Temp. (°C.) | % 143a | % 133a | % 123 | % 113a | % 112a | % HCE |
|---|---|---|---|---|---|---|---|
| 1 | 250 | 95.3 | 2.2 | 0.5 | 0.1 | 0.3 | 0.6 |
| 2 | 300 | 84.8 | 4.3 | 2.3 | 2.9 | 1.8 | 1.6 |

TABLE 5-continued

| Time (hr) | Temp. (°C.) | % 143a | % 133a | % 123 | % 113a | % 112a | % HCE |
|---|---|---|---|---|---|---|---|
| 3 | 350 | 53.8 | 4.5 | 4.5 | 25.0 | 6.4 | 2.2 |
| 4 | 375 | 30.9 | 3.1 | 3.7 | 48.9 | 9.7 | 0.9 |
| 5 | 375 | 25.4 | 2.6 | 3.4 | 56.5 | 9.1 | 0.7 |

Minor amounts of other products including $CClF_3$, $CCl_3F$, $CF_3CCl_2F$, $CCl_2F_2$, $CCl_4$, $CClF_2CHCl_2$, and $CCl_2FCCl_3$ were also found.

EXAMPLE 6

Chlorination Using $CuCl_2$/Carbon

The general chlorination procedure described above was followed. A solution of $CuCl_2 \cdot 2H_2O$ (25.1 g) in water (70 mL) was poured over 40 mL of commercial carbon granules (0.32 cm pellets). The resulting mixture was allowed to stand at room temperature for 1 hour and was then placed in a vacuum oven at 110° C. for 16 to 24 hours to remove the water. The catalyst was then placed in the reactor and heated under a nitrogen flow to 350° C. The temperature was reduced to 225° C. and the catalyst was heated under a nitrogen flow overnight. The flows of chlorine and 143a were started. The molar ratio of chlorine to 143a was 4:1 except for the 12 hour sample where it was 6:1 and the 13 hour sample where it was 1. The contact time was 30 seconds. The reactor effluent was analyzed as described above. The results are shown in Table 6.

TABLE 6

| Time (hr) | Temp. (°C.) | % 143a | % 133a | % 123 | % 113a | % 112a | % HCE |
|---|---|---|---|---|---|---|---|
| 1 | 225 | 98.0 | 1.2 | 0.2 | <0.1 | <0.1 | — |
| 2 | 250 | 95.2 | 2.2 | 0.6 | 0.4 | 0.6 | 0.2 |
| 3 | 275 | 89.0 | 3.1 | 1.5 | 2.7 | 1.7 | 0.9 |
| 4 | 300 | 75.0 | 3.6 | 2.2 | 10.3 | 4.4 | 2.4 |
| 5 | 325 | 53.2 | 3.3 | 2.3 | 25.0 | 8.4 | 4.3 |
| 7 | 350 | 30.8 | 2.5 | 2.1 | 57.5 | 2.7 | 2.4 |
| 8 | 375 | 10.4 | 1.0 | 1.1 | 82.3 | 3.2 | 0.8 |
| 12 | 375 | 7.0 | 0.8 | 0.9 | 83.5 | 4.2 | 1.2 |
| 13 | 375 | 7.3 | 0.8 | 0.9 | 86.5 | 2.8 | 0.6 |

Minor amounts of other products including $CClF_3$, $CCl_2F_2$, $CClF_2CH_2Cl$, $CCl_4$, $CClF_2CHCl_2$, $CCl_2FCClF_2$, $CCl_2=CCl_2$, and $CCl_2FCCl_3$ were also found.

EXAMPLE 7

Chlorination Using $CrCl_3$/Carbon

The general chlorination procedure described above was followed. A commercial 20% $CrCl_3$/carbon catalyst (12.9 g, 30 mL) was placed in the reactor and treated with HF (50 cc/min.)/$N_2$ (50 cc/min.), at 175° C. for 0.25 hr. After this time, the gaseous flows were changed to HF (80 cc/min.)/$N_2$ (20 cc/min.), and the temperature was increased to 400° C. over 2 hours and maintained at 400° C. for about 0.25 hours. The temperature was then reduced to 250° C., the HF/$N_2$ flow was stopped and the flows of chlorine and 143a were started at 250° C. The molar ratio of chlorine to 143a was 4:1 except for the 22 hour sample where it was 2:1. The contact time was 30 seconds. The reactor effluent was analyzed as described above. The results are shown in Table 7.

TABLE 7

| Time (hr) | Temp. (°C.) | % 143a | % 133a | % 114[1] | % 114a[2] | % 123 | % 113[3] | % 113a | % 122[4] | % 112[5] | % 112a | % 111[6] | % HCE |
|---|---|---|---|---|---|---|---|---|---|---|---|---|---|
| 3 | 250 | 13.5 | 22.4 | 0.4 | 0.2 | 3.6 | 4.0 | 0.7 | 5.2 | 23.5 | 11.5 | 11.3 | 2.6 |
| 17 | 270 | 6.0 | 17.9 | 0.7 | 0.4 | 3.8 | 7.0 | 1.2 | 4.3 | 32.6 | 11.0 | 11.4 | 2.5 |
| 19 | 310 | <0.1 | 7.1 | 1.5 | 2.4 | 4.3 | 18.6 | 5.6 | 0.7 | 28.8 | 14.4 | 12.5 | 3.0 |
| 21 | 350 | 0.0 | 0.9 | 2.3 | 6.6 | 1.9 | 25.5 | 10.3 | 0.1 | 18.7 | 15.5 | 11.9 | 5.2 |
| 22 | 350 | 6.9 | 7.3 | 3.1 | 3.8 | 3.8 | 23.6 | 1.6 | 0.6 | 5.9 | 3.7 | 0.8 | 0.0 |

[1] 114 = $CClF_2CClF_2$
[2] 114a = $CF_3CCl_2F$
[3] 113 = $CClF_2CCl_2F$
[4] 122 = $CClF_2CHCl_2$
[5] 112 = $CCl_2FCCl_2F$
[6] 111 = $CCl_2FCCl_3$

Minor amounts of other products including $CClF_3$, $CF_3CClF_2$, $CF_3CHClF$ and $CClF_2CHClF$ were also found. Additionally the 22 hr sample also contained 5.5% $CCl_2=CClF$, 2.2% $CHCl=CCl_2$ and 27.8% $CCl_2=CCl_2$.

COMPARATIVE EXAMPLE

Chlorination Using HCl Washed Silicon Carbide

The general chlorination procedure described above was followed. Silicon carbide was soaked with stirring in 1% $HNO_3$, washed with water and dried. The dried, acid-washed catalyst (49.0 g, 30 mL of 14×20 mesh granules) was placed in the reactor and heated under a nitrogen flow to 250° C. The flows of chlorine and 143a were then started. The molar ratio of chlorine to 143a was 4:1 and the contact time was 30 seconds. The reactor effluent was analyzed as described above. The results are shown in Table B.

TABLE B

| Time (hr) | Temp. (°C.) | % 143a | % 133a | % 123 | % 113a | % 122 | % 112a | % 111 | % PCE[1] | % HCE |
|---|---|---|---|---|---|---|---|---|---|---|
| 2 | 250 | 82.2 | 4.1 | 1.2 | 0.2 | 1.4 | 0.4 | 1.6 | 2.5 | 1.3 |
| 3 | 275 | 89.4 | 2.1 | 0.4 | <0.1 | 0.6 | 0.1 | 0.8 | 1.0 | 3.6 |
| 4 | 300 | 88.2 | 2.3 | 0.5 | 0.1 | 0.6 | 0.1 | 0.5 | 1.0 | 4.4 |
| 5 | 350 | 67.6 | 6.5 | 5.1 | 3.6 | 1.3 | 1.4 | 1.3 | 3.0 | 7.1 |
| 6 | 350 | 74.7 | 6.9 | 4.9 | 3.0 | 1.4 | 0.9 | 0.8 | 1.6 | 3.2 |

[1] PCE = perchloroethylene (i.e., $CCl_2=CCl_2$)

Other products including $CClF_2CH_3$, $CClF_2CH_2Cl$, $CClF_2CHCl_2$, $CCl_2FCCl_2F$ and $CCl_2FCHCl_2$ were also found.

EXAMPLE 8

Chlorination Using 2% Pt/Carbon

The general chlorination procedure described above was followed. A 2% Pt/carbon catalyst (12.5 g, 30 mL) prepared by known art procedures using platinum (IV) chloride and Catalyst A (i.e., HCl-washed carbon) was placed in the reactor, heated under a nitrogen flow to 400° C. (at which temperature the catalyst was maintained for 1 hour) and then cooled to 300° C. and brought to the temperatures shown in Table 8. The flows of chlorine and 143a were started at 300° C. The molar ratio of chlorine to 143a was 4:1 and the contact time was 30 seconds. The reactor effluent was analyzed as described above. The results are shown in Table 8.

TABLE 8

| Temp. °C. | % 143a | % 133a | % 114a | % 123 | % 113a | % 112a |
| --- | --- | --- | --- | --- | --- | --- |
| 300 | 30.4 | 2.4 | 3.2 | 1.6 | 56.1 | 3.7 |
| 325 | 30.6 | 2.4 | 2.6 | 1.8 | 52.2 | 5.1 |
| 350 | 22.6 | 2.0 | 3.2 | 1.7 | 55.5 | 8.6 |

Minor amounts of other products including $CF_3CH_2F$, $CF_3CClF_2$, $CHF_2CClF_2$, $CClF_2CHClF$, $C_2HCl_2F$, $CCl_2FCClF_2$ and $CClF_2CHCl_2$ were also found.

EXAMPLE 9

Chlorination Using 2% Ru/Carbon

The general chlorination procedure described above was followed. A 2% ruthenium/carbon catalyst (12.1 g, 30 mL) prepared by known art procedures using ruthenium chloride and Catalyst A (i.e., HCl-washed carbon) was placed in the reactor, heated under a nitrogen flow to 400° C. (at which temperature the catalyst was maintained for 1 hour) and then cooled to 300° C. and brought to the temperatures shown in Table 9. The flows of chlorine and 143a were started at 300° C. The molar ratio of chlorine to 143a was 4:1 and the contact time was 30 seconds. The reactor effluent was analyzed as described above. The results are shown in Table 9.

TABLE 9

| Temp. °C. | % 143a | % 133a | % 114a | % 123 | % 113a | % 112a |
| --- | --- | --- | --- | --- | --- | --- |
| 300 | 76.1 | 2.2 | 1.5 | 1.1 | 15.7 | 1.0 |
| 325 | 32.5 | 1.5 | 3.0 | 0.6 | 52.5 | 7.9 |
| 350 | 8.9 | 0.0 | 3.9 | 0.0 | 70.1 | 13.8 |

Minor amounts of other products including $CF_3CH_2F$, $CF_3CClF_2$, $CHF_2CClF_2$, $CClF_2CHClF$, $C_2HCl_2F$, $CCl_2FCClF_2$ and $CClF_2CHCl_2$ were also found.

EXAMPLE 10

Chlorination Using 2% Rh/Carbon

The general chlorination procedure described above was followed. A 2% Rh/carbon catalyst (12.8 g, 30 mL) prepared by known art procedures using $RhCl_3 \cdot 3H_2O$ chloride and Catalyst A (i.e., HCl-washed carbon) was placed in the reactor, heated under a nitrogen flow to 400° C. (at which temperature the catalyst was maintained for 1 hour) and then cooled to 300° C. and brought to the temperatures shown in Table 10. The flows of chlorine and 143a were started at 300° C. The molar ratio of chlorine to 143a was 4:1 and the contact time was 30 seconds. The reactor effluent was analyzed as described above. The results are shown in Table 10.

TABLE 10

| Temp. °C. | % 143a | % 133a | % 114a | % 123 | % 113a | % 112a |
| --- | --- | --- | --- | --- | --- | --- |
| 300 | 58.8 | 2.6 | 2.0 | 1.6 | 29.5 | 2.0 |
| 325 | 45.7 | 0.3 | 2.4 | 1.9 | 38.8 | 4.3 |
| 350 | 11.5 | 0.0 | 3.3 | 0.6 | 69.2 | 11.7 |

Minor amounts of other products including $CF_3CH_2F$, $CF_3CClF_2$, $CHF_2CClF_2$, $CClF_2CHClF$, $C_2HCl_2F$, $CCl_2FCClF_2$ and $CClF_2CHCl_2$ were also found.

EXAMPLE 11

Chlorination Using HCl Washed Carbon and HF

The general chlorination procedure described above was followed. The same catalyst as Example 2 was used. The molar ratio of chlorine to 143a to HF was 4:1:4 and the contact time was 30 seconds. The reactor effluent was analyzed as described above. The results are shown in Table 11.

TABLE 11

| Time (hr) | Temp. °C. | % 143a | % 114a | % 113 | % 113a | % 112 | % 112a |
| --- | --- | --- | --- | --- | --- | --- | --- |
| 24 | 375 | 0.5 | 6.2 | 2.3 | 83.2 | 1.1 | 5.4 |

Minor amounts of other products including $CClF_3$, $CF_3CClF_2$, $CCl_2FCClF_2$, $CCl_2F_2$, $CCl_2FCCl_2F$, and $CCl_2FCCl_3$ were also found.

EXAMPLE 12

Chlorination Using Unwashed Carbon and HF

The general chlorination procedure described above was followed. The same catalyst as Example 4 was used. The molar ratio of chlorine to 143a to HF was 4:1:4 and the contact time was 30 seconds. The reactor effluent was analyzed as described above. The results are shown in Table 12.

TABLE 12

| Time (hr) | Temp. °C. | % 143a | % 114a | % 113 | % 113a | % 112 | % 112a |
| --- | --- | --- | --- | --- | --- | --- | --- |
| 13 | 375 | 0.8 | 6.1 | 1.9 | 83.9 | 1.1 | 4.9 |
| 23 | 375 | 0.9 | 6.2 | 2.1 | 83.6 | 1.1 | 5.1 |
| 26 | 400 | <0.1 | 9.7 | 4.2 | 77.2 | 1.5 | 5.9 |

Minor amounts of other products including $CClF_3$, $CF_3CClF_2$, $CCl_2F_2$, and $CCl_2FCCl_3$ were also found.

EXAMPLE 13

Chlorination Using Carbon

In this example, all parts and percentages are by weight and all temperatures are degrees Celsius. All product compositions are relative area based on gas chromatographic analyses, and are uncorrected for relative response. Activated carbon (3 g) was loaded into a Vycor® reactor (1 cm diameter × 10 cm long). The reactor was heated in a split-tube furnace. The temperature was adjusted to the levels indicated in Table 13 below, and the flows of $Cl_2$ (30 cc/min.), $N_2$ (5 cc/min.), and HFC-143a (10 mL/min.) over the catalyst were then initiated. The reactor effluent was sampled on line by a Varian-6000 gas chromatograph using a 10 foot × ⅛" ID column containing Krytox® perfluorinated polyether on an inert support and a helium flow of 20-35 cc/minute. Gas chromatographic conditions were 70° C. for 6.5 minutes followed by temperature programming to 180° C. at a rate of 35° C./minute. A flame ionization detector was used to provide relative areas.

TABLE 13

| T °C. | 143a | 133a | 123 | 113a |
|---|---|---|---|---|
| 172 | 67 | 1.3 | | |
| 209 | 73 | 2.6 | | |
| 232 | 66 | 0.9 | 2.4 | 0.1 |
| 261 | 55 | 1.2 | 0.2 | 9.6 |
| 283 | 44 | 1.2 | — | 17 |
| 300 | 35 | 1.1 | — | 31 |
| 350 | 11 | 0.6 | — | 46 |

Particular embodiments of the invention are included in the examples. Other embodiments will become apparent to those skilled in the art from a consideration of the specification or practice of the invention disclosed herein. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the following claims.

What is claimed is:

1. A process for producing 1,1,1-trichloro-2,2,2-trifluoroethane comprising the step of: contacting a gaseous mixture containing at least one compound having the formula $CH_xCl_{3-x}CF_3$, where x is an integer from 1 to 3 and chlorine with a catalyst at a temperature of from about 225° C. to about 450° C., wherein the catalyst is selected from the group consisting of carbon catalysts and catalysts of metal halide supported on carbon wherein the metal halide is a chloride and/or fluoride of a metal selected from the group consisting of zinc, copper, chromium, ruthenium, rhodium, platinum, and mixtures thereof.

2. The process of claim 1 wherein the catalyst consists essentially of carbon.

3. The process of claim 2 wherein the carbon is acid-washed.

4. The process of claim 3 wherein the ash content of the carbon is about 0.5 percent by weight, or less.

5. The process of claim 1 wherein the catalyst comprises acid-washed carbon.

6. The process of claim 1 wherein the catalyst is a catalyst of metal halide supported on carbon.

7. The process of claim 6 wherein the carbon is washed with an acid.

8. The process of claim 6 wherein the metal halide is a zinc chloride and/or fluoride.

9. The process of claim 6 wherein the metal halide is a copper chloride and/or fluoride.

10. The process of claim 6 wherein the metal halide is a chromium chloride and/or fluoride.

11. The process of claim 6 wherein the metal halide is a ruthenium chloride and/or fluoride.

12. The process of claim 6 wherein the metal halide is a rhodium chloride and/or fluoride.

13. The process of claim 6 wherein the metal halide is a platinum chloride and/or fluoride.

14. The process of claim 1 wherein the temperature is from about 350° C. to 400° C.

15. The process of claim 1 wherein the catalyst is an activated carbon catalyst.

16. The process of claim 1 wherein the at least one compound having the formula $CH_xCL_{3-x}CF_3$ is $CH_3CF_3$.

17. The process of claim 1 wherein the mole ratio of chlorine to the organic starting material is between about 1.5:1 and 10:1.

* * * * *

UNITED STATES PATENT AND TRADEMARK OFFICE
CERTIFICATE OF CORRECTION

PATENT NO. : 5,120,883

DATED : June 9, 1992

INVENTOR(S) : Rao, et al.

Page 1 of 2

It is certified that error appears in the above-identified patent and that said Letters Patent is hereby corrected as shown below:

At Column 1, line 32 - "CF3CCl3" should read --$CF_3CCl_3$--.

At Column 1, line 48 - "CF3CCl2F" should read --$CF_3CCl_2F$--.

At Column 2, line 56 et seq. - "Darcor TM, Nucharr TM, Columbia SBV TM, Columbia MBV TM, Columbia MBQ TM, Columbia JXC TM, Columbia CXC TM, Calgon PCB TM, and Barnaby Cheny NB TM" should read --Darco$^{TM}$, Nuchar$^{TM}$, Columbia SBV$^{TM}$, Columbia MBV$^{TM}$, Columbia MBQ$^{TM}$, Columbia JXC$^{TM}$, Columbia CXC$^{TM}$, Calgon PCB$^{TM}$, and Barnaby Cheny NB$^{TM}$--.

At Column 3, line 11 - "1.5 to moles" --1.5 to 10 moles--.

At Column 3, line 14 - "0°C to 400°C" should read --300°C to 400°C--.

At Column 3, line 39 - "1,1,1-Trichloro-2,2,2trifluoroethane" should read --1,1,1-Trichloro-2,2,2-trifluoroethane--.

At Column 3, line 55 - "20°C for" should read --120°C for--.

At Column 4, line 33 - "0.5" IOD" should read --0.5" ID--.

UNITED STATES PATENT AND TRADEMARK OFFICE
CERTIFICATE OF CORRECTION

PATENT NO. : 5,120,883

DATED : June 9, 1992

INVENTOR(S) : Rao, et al.

It is certified that error appears in the above-identified patent and that said Letters Patent is hereby corrected as shown below:

At Column 4, line 51 - "Hcl" should read --HCl--.

At Column 7, line 42 - "it was 1." should read --it was 8:1--.

At Column 12, line 32 (Claim 16) - "$CH_xCL3_{-x}CF3$" should read --$CH_xCl3_{-x}CF3$--.

Signed and Sealed this

Seventeenth Day of August, 1993

Attest:

BRUCE LEHMAN

Attesting Officer

Commissioner of Patents and Trademarks